US012310478B2

(12) United States Patent
Jiang (10) Patent No.: US 12,310,478 B2
(45) Date of Patent: May 27, 2025

(54) FAR INFRARED HAIR DRYER (71) Applicant: Dongguan Meisheng Intelligent Technology Co., Ltd, Dongguan (CN)

(72) Inventor: Junmin Jiang, Dongguan (CN)

(73) Assignee: Dongguang Meisheng Intelligent Technology Co.,Ltd, Dongguan (CN)

( * ) Notice: Subject to any disclaimer, the term of this patent is extended or adjusted under 35 U.S.C. 154(b) by 143 days.

(21) Appl. No.: 18/302,026

(22) Filed: Apr. 18, 2023

(65) Prior Publication Data
US 2023/0329410 A1 Oct. 19, 2023

(30) Foreign Application Priority Data

Apr. 18, 2022 (CN) .......................... 202210407051.0

(51) Int. Cl.
*A45D 20/10* (2006.01)
(52) U.S. Cl.
CPC ........ *A45D 20/10* (2013.01); *A45D 2200/205* (2013.01)
(58) Field of Classification Search
CPC .......................... A45D 20/10; A45D 2200/205
USPC ...................................................... 34/95–100
See application file for complete search history.

(56) References Cited

U.S. PATENT DOCUMENTS

| 2,335,553 | A | * | 11/1943 | Valverde | A45D 20/46 34/100 |
| 4,019,260 | A | * | 4/1977 | Levy | A45D 20/122 239/389 |
| 6,481,116 | B1 | * | 11/2002 | Slingo | A45D 20/12 392/375 |
| 6,798,982 | B2 | * | 9/2004 | Ryu | A45D 20/10 34/97 |

(Continued)

FOREIGN PATENT DOCUMENTS

| AU | 2021299816 A1 | * | 2/2023 | ............. A45D 20/10 |
| CN | 114869038 A | * | 8/2022 | ............. A45D 20/10 |

(Continued)

OTHER PUBLICATIONS

EPO, Decision to grant a European patent pursuant to Article 97(1) EPC for EP23168358.2, Jul. 11, 2024.

(Continued)

*Primary Examiner* — Stephen M Gravini
(74) *Attorney, Agent, or Firm* — Hemisphere Law, PLLC; Zhigang Ma (57) ABSTRACT

The present disclosure relates to the technical field of hairdressing, in particular to, a novel far infrared hair dryer, including: a body, which is provided with a fluid inlet formed in a rear end and a fluid outlet formed in a front end; a fluid flowing path, which is arranged in the body and extends from the fluid inlet to the fluid outlet; a conveying mechanism, which is arranged in the fluid flowing path and drives a fluid to flow from the fluid inlet to the fluid outlet;

(Continued)

and a heating mechanism, which is arranged in the fluid flowing path and is used for heating the fluid in the fluid flowing path. The novel far infrared hair dryer can improve the compactness of the overall structure to the maximum extent, ensure that air is blown out smoothly, and reduce the obstruction to the air, thus reducing noise.

9 Claims, 6 Drawing Sheets

(56) References Cited

U.S. PATENT DOCUMENTS

| | | | | |
|---|---|---|---|---|
| 8,272,142 | B2 * | 9/2012 | Hall | A45D 20/12 |
| | | | | 132/271 |
| 9,414,662 | B2 * | 8/2016 | Moloney | A45D 20/00 |
| 9,420,864 | B2 * | 8/2016 | Gammack | A45D 20/10 |
| 9,420,865 | B2 * | 8/2016 | Gammack | A45D 20/12 |
| 11,517,091 | B2 * | 12/2022 | Conrad | A45D 20/50 |
| 11,641,918 | B2 * | 5/2023 | Jeong | A45D 20/12 |
| | | | | 34/97 |
| 11,713,924 | B2 * | 8/2023 | Zielinski | F26B 23/04 |
| | | | | 34/92 |
| 2011/0079239 | A1 | 4/2011 | Hall | |
| 2016/0213122 | A1 | 7/2016 | Sakuma et al. | |
| 2019/0269219 | A1 | 9/2019 | Xiao | |
| 2023/0329410 | A1 * | 10/2023 | Jiang | A45D 20/10 |

FOREIGN PATENT DOCUMENTS

| | | | | |
|---|---|---|---|---|
| EP | 4265149 | A1 * | 10/2023 | A45D 20/10 |
| GB | 2515814 | A  * | 1/2015 | A45D 20/10 |
| JP | 2023158661 | A  * | 10/2023 | A45D 20/10 |
| WO | WO-2015150720 | A1 * | 10/2015 | A45D 20/08 |

OTHER PUBLICATIONS

European patent No. EP4265149 (Application No. 23168358.2), issued Aug. 7, 2024.

* cited by examiner

FAR INFRARED HAIR DRYER

TECHNICAL FIELD

The present disclosure relates to the technical field of hairdressing, in particular to, a novel far infrared hair dryer.

BACKGROUND

A hair dryer is a personal care small home appliance that can quickly blow hairs to dry. The hair dryer heats air by a heating wire, so that hairs can be blown to dry quickly, which shortens the time of drying hairs and facilitates the life. Far infrared rays have high seepage force and radiation force, have an outstanding temperature control effect and resonance effect, and are easily absorbed by objects and converted into internal energy of the objects. After the far infrared rays are absorbed by the body of a user, water molecules in the body generate resonance to be activated, thereby improving the binding force between the molecules, thus activating biological macromolecules such as proteins. Therefore, biological cells are at the highest vibration level. Due to the resonance effect generated by the biological cells, far infrared thermal energy can be transmitted to deeper subcutaneous parts of the user, so that temperatures of deeper subcutaneous layers rise, causing generated warmth to be radiated from the inside to the outside. This intensity of action dilates capillaries, promotes blood circulation, strengthens metabolism between various tissues, improves the regeneration abilities of the tissues, improves the immunocompetence of organs, and regulates a hysterical mental state, thereby achieving a medical care effect. If negative ions can be released during hairdressing, static electricity can be neutralized, open squamous superficial layers can be flattened, and hairlines can be repaired and smoothed, thereby achieving a hair protection effect.

In order to make air from a hair dryer generate negative ions and far infrared waves, to bring physiotherapy and beautifying effects to hairs, a ceramic heater would be arranged between a corresponding heating mechanism and an air outlet in the hair dryer. The ceramic heater has a radiance of generally greater than 85% at a room temperature (25° C. to 150° C.), which has an efficient photothermal conversion efficiency and can generate negative ions. However, the existing ceramic heater is mainly arranged in a honeycomb structure in front of the heating mechanism. After the ceramic heater and the heating mechanism are combined, the structure is not compact enough, resulting in an increase in the overall volume of the hair dryer. Moreover, after the ceramic heater and the heating mechanism are combined, an internal fluid channel is complex, which will significantly obstruct air from being blown out and make the hair dryer noisy during use. It is necessary to propose a new technical solution to address the aforementioned issues.

SUMMARY

In order to overcome the above deficiencies, the present disclosure aims to provide a technical solution capable of addressing the aforementioned issues.

A novel far infrared hair dryer includes:
a body, which is provided with a fluid inlet formed in a rear end and a fluid outlet formed in a front end;
a fluid flowing path, which is arranged in the body and extends from the fluid inlet to the fluid outlet;
a conveying mechanism, which is arranged in the fluid flowing path and drives a fluid to flow from the fluid inlet to the fluid outlet; and
a heating mechanism, which is arranged in the fluid flowing path and is used for heating the fluid in the fluid flowing path,
wherein the fluid flowing path is provided with an annular cavity at a front section, and the fluid outlet is of an annular orifice structure abutted to the annular cavity; the heating mechanism is arranged in the annular cavity; and the heating mechanism includes an annular heat radiation assembly wound in the annular cavity in a suspended manner, an annular heater embedded into the annular heat radiation assembly, a far infrared ceramic coating layer arranged on an outer surface of the annular heat radiation assembly, and a fixed support that is fixed in the annular cavity and is used for supporting the annular heat radiation assembly.

Preferably, a first pipe body abutted to the fluid inlet and a second pipe body abutted to the fluid outlet are arranged in the body; the first pipe body and the second pipe body are connected with each other, so that the fluid flowing path is formed inside the first pipe body and the second pipe body; the conveying mechanism is arranged in the first pipe body; and the heating mechanism is arranged in the second pipe body.

Preferably, a guide component extending into the second pipe body is arranged in the middle of the fluid outlet; the fluid outlet is formed into the annular orifice structure through the guide component; and the annular cavity is formed inside the second pipe body through the guide component.

Preferably, a diameter of the first pipe body is less than a diameter of the second pipe body; a bevel transition end is arranged between the first pipe body and the second pipe body; and the first pipe body is hermetically connected with the second pipe body through the bevel transition end.

Preferably, the annular heat radiation assembly includes a first annular body and a second annular body sleeving the first annular body; the annular heater resists against and is fixed between the first annular body and the second annular body; a plurality of uniformly arranged radiator fins are arranged around an inner side of the first annular body and an outer side of the second annular body; the far infrared ceramic coating layer is coated on the radiator fins; and the radiator fins are parallel to the fluid flowing path.

Preferably, the second annular body includes two semicircular portions which are in abutting fit with each other; matching portions are arranged at mutually abutted positions of the two semicircular portions; and screw structures are arranged on the matching portions to lock the two semicircular portions.

Preferably, a wiring gap is formed in a rear end of one semicircular portion, and the annular heater is connected to a wire through the wiring gap.

Preferably, the fixed support includes several fixing assemblies; the several fixing assemblies are circumferentially uniformly arranged on the annular heat radiation assembly in a surrounding manner; and the fixing assemblies are abutted between the second pipe body and the guide component.

Preferably, the fixing assemblies include a first fixing plate and a second fixing plate; fixing portions are arranged at upper ends and lower ends of the first fixing plate and the second fixing plate; the first fixing plate and the second fixing plate are fixedly connected through the fixing portions, so that a closed-loop structure surrounding the annular heat radiation assembly is formed between the first fixing plate and the second fixing plate; the first fixing plate is located on an inner side of the annular heat radiation assembly and is abutted to the guide component; and the second fixing plate is located on an outer side of the annular heat radiation assembly and is abutted to the second pipe body.

Preferably, a clamping gap is formed in an end portion of each second fixing plate abutted to the second pipe body; the plurality of fixing assemblies are fixedly sleeved with heat insulation rings through the clamping gaps; and the heat insulation rings are in abutting fit with the inner side of the second pipe body.

Compared with the prior art, the present disclosure has the following beneficial effects:

The fluid flowing path of the traditional hair dryer is further improved: the section corresponding to the fluid outlet is designed to be the annular cavity, so that a negative pressure can be generated in the middle of the fluid outlet when the hair dryer works, to achieve an eddy current effect to improve a guided air discharge effect. Meanwhile, an annular air outlet can reduce concentration of far infrared waves in the middle of the air outlet, so that the far infrared waves can be radiated annularly, to improve the uniformity of heat radiation and uniformly supply negative ions, which avoids injuries to the scalp caused by excessive local radiation during use. Thus, more efficient medical care and a hair care effect can be provided for users.

The annular heat radiation assembly, the annular heater, the far infrared ceramic coating layer, and the fixed support are assembled into the heating mechanism. The annular heater is used for being powered on to generate heat and thermal energy. The annular heat radiation assembly is used to transfer the heat. The outer surface of the annular heat radiation assembly is coated with one far infrared ceramic coating layer which is prepared by mixing far infrared ceramic powder with a high-temperature-resistant adhesive and is then brushed on the annular heat radiation assembly, so that when the heater generates heat, the heat can be radiated through the annular heat radiation assembly, to dry hairs. In addition, the heat radiation of the annular heat radiation assembly is also fully used to make a temperature of the far infrared ceramic coating layer reach 25° C. to 150° C. to generate negative ions and far infrared waves. By the arrangement of the fixed support, the annular heat radiation assembly can be wound in the annular cavity in the suspended manner, which can improve the compactness of the overall structure to the maximum extent, ensure that air is blown out smoothly, and reduce the obstruction to the air, thus reducing noise. A user feels comfortable with such a small hair dryer.

The additional aspects and advantages of the prevent disclosure will be provided in the following descriptions, part of which will become apparent from the following descriptions or be learned through the practice of the prevent disclosure.

BRIEF DESCRIPTION OF THE DRAWINGS

To describe the embodiments of the present disclosure or the technical solutions in the existing art more clearly, drawings required to be used in the embodiments or the illustration of the existing art will be briefly introduced below. Obviously, the drawings in the illustration below are only some embodiments of the present disclosure. Those ordinarily skilled in the art also can acquire other drawings according to the provided drawings without doing creative work.

Reference numerals and names in the drawings are as follows:

body 10, fluid inlet 11, fluid outlet 12, first pipe body 13, second pipe body 14, guide component 15, bevel transition end 16, fluid flowing path 20, annular cavity 21, conveying mechanism 30, heating mechanism 40, annular heat radiation assembly 41, first annular body 411, second annular body 412, radiator fin 413, semi-circular portion 414, wiring gap 415, annular heater 42, fixed support 44, fixing assembly 441, first fixing plate 442, second fixing plate 443, fixing portion 444, clamping gap 445, heat insulation ring 45, handheld portion 50, main control board 51, cable 52, and fixing ring 53.

DETAILED DESCRIPTION OF THE EMBODIMENTS

The technical solutions in the embodiments of the present disclosure will be clearly and completely described below. Apparently, the described embodiments are only a part of the embodiments of the present disclosure, rather than all the embodiments. All other embodiments obtained by those of ordinary skill in the art based on the embodiments in the present disclosure without creative work shall fall within the protection scope of the present disclosure.

Referring to FIG. 1 to FIG. 6, in this embodiment of the present disclosure, a novel far infrared hair dryer includes:

a body 10, which is provided with a fluid inlet 11 formed in a rear end and a fluid outlet 12 formed in a front end, wherein a handheld portion 50 is arranged at a lower end of the body 10;

a fluid flowing path 20, which is arranged in the body 10 and extends from the fluid inlet 11 to the fluid outlet 12;

a conveying mechanism 30, which is arranged in the fluid flowing path 20 and drives a fluid to flow from the fluid inlet 11 to the fluid outlet 12; and a heating mechanism 40, which is arranged in the fluid flowing path 20 and is used for heating the fluid in the fluid flowing path 20.

The fluid flowing path 20 is provided with an annular cavity 21 at a front section, and the fluid outlet 12 is of an annular orifice structure abutted to the annular cavity 21. The heating mechanism 40 is arranged in the annular cavity 21. The heating mechanism 40 includes an annular heat radiation assembly 41 wound in the annular cavity 21 in a suspended manner, an annular heater 42 embedded into the annular heat radiation assembly 41, a far infrared ceramic coating layer (not shown in the figure) arranged on an outer surface of the annular heat radiation assembly 41, and a fixed support 44 that is fixed in the annular cavity 21 and is used for supporting the annular heat radiation assembly 41.

In the present disclosure, the fluid flowing path 20 of the traditional hair dryer is further improved: the section corresponding to the fluid outlet 12 is designed to be the annular cavity 21, so that a negative pressure can be generated in the middle of the fluid outlet 12 when the hair dryer works, to achieve an eddy current effect to improve a guided air discharge effect. Meanwhile, an annular air outlet can reduce concentration of far infrared waves in the middle of the air outlet, so that the far infrared waves can be radiated annularly, to improve the uniformity of heat radiation and uniformly supply negative ions, which avoids injuries to the scalp caused by excessive local radiation during use. Thus, more efficient medical care and a hair care effect can be provided for users.

According to the annular cavity 21, the annular heat radiation assembly 41, the annular heater 42, the far infrared ceramic coating layer, and the fixed support 44 are assembled into the heating mechanism 40. The annular heater 42 is used for being powered on to generate heat and thermal energy. The annular heat radiation assembly 41 is used to transfer the heat. The outer surface of the annular heat radiation assembly 41 is coated with one far infrared ceramic coating layer which is prepared by mixing far infrared ceramic powder with a high-temperature-resistant adhesive and is then brushed on the annular heat radiation assembly 41, so that when the heater generates heat, the heat can be radiated through the annular heat radiation assembly 41, to dry hairs. In addition, the heat radiation of the annular heat radiation assembly 41 is also fully used to make a temperature of the far infrared ceramic coating layer reach 25° C. to 150° C. to generate negative ions and far infrared waves. By the arrangement of the fixed support 44, the annular heat radiation assembly 41 can be wound in the annular cavity 21 in the suspended manner, which can improve the compactness of the overall structure to the maximum extent, ensure that air is blown out smoothly, and reduce the obstruction to the air, thus reducing noise. A user feels comfortable with such a small hair dryer.

Figure 2:
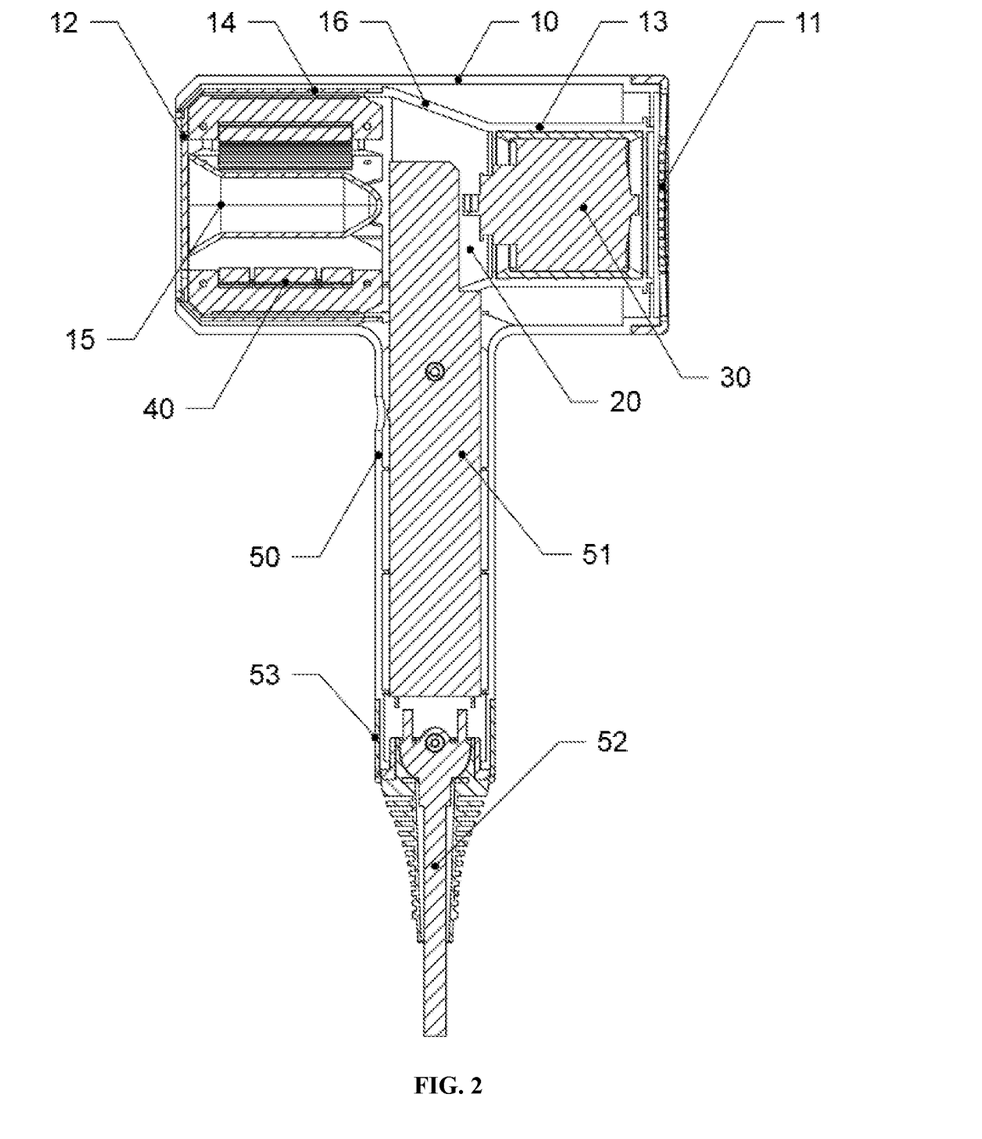
FIG. 2 is a schematic diagram of a sectional structure of the present disclosure.
Figure 3:
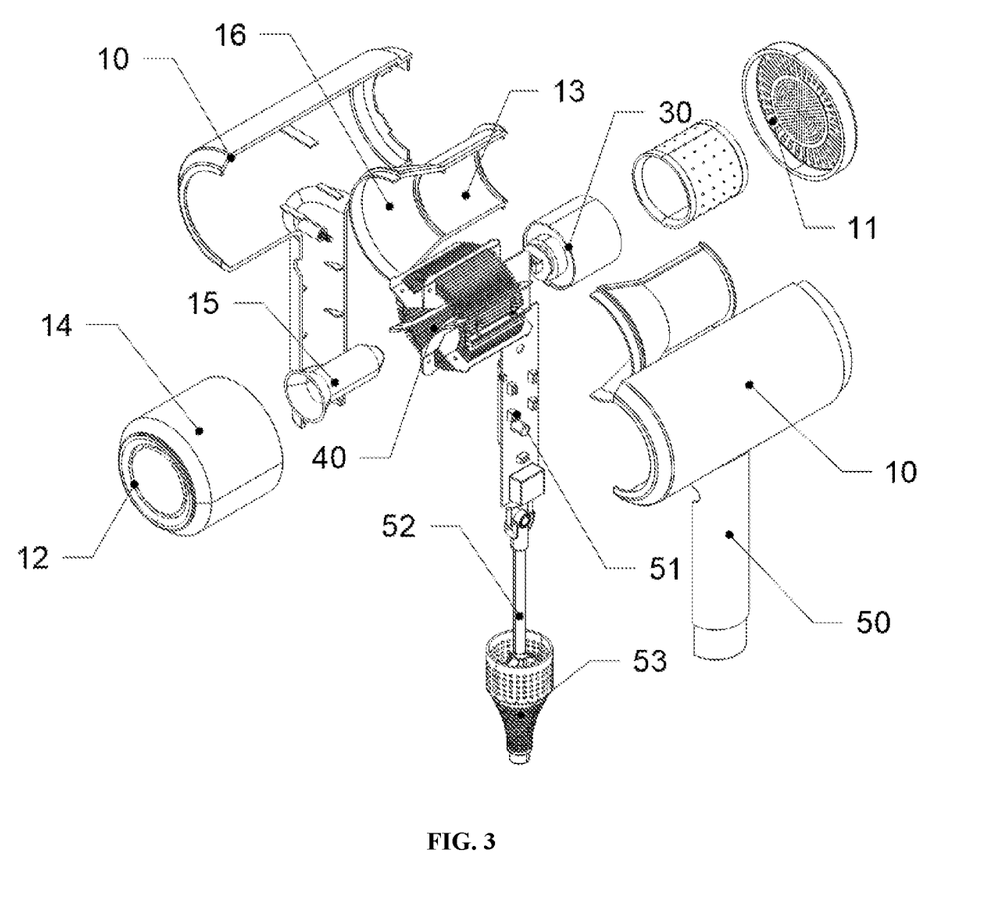
FIG. 3 is a schematic diagram of an exploded structure of the present disclosure.
Figure 5:
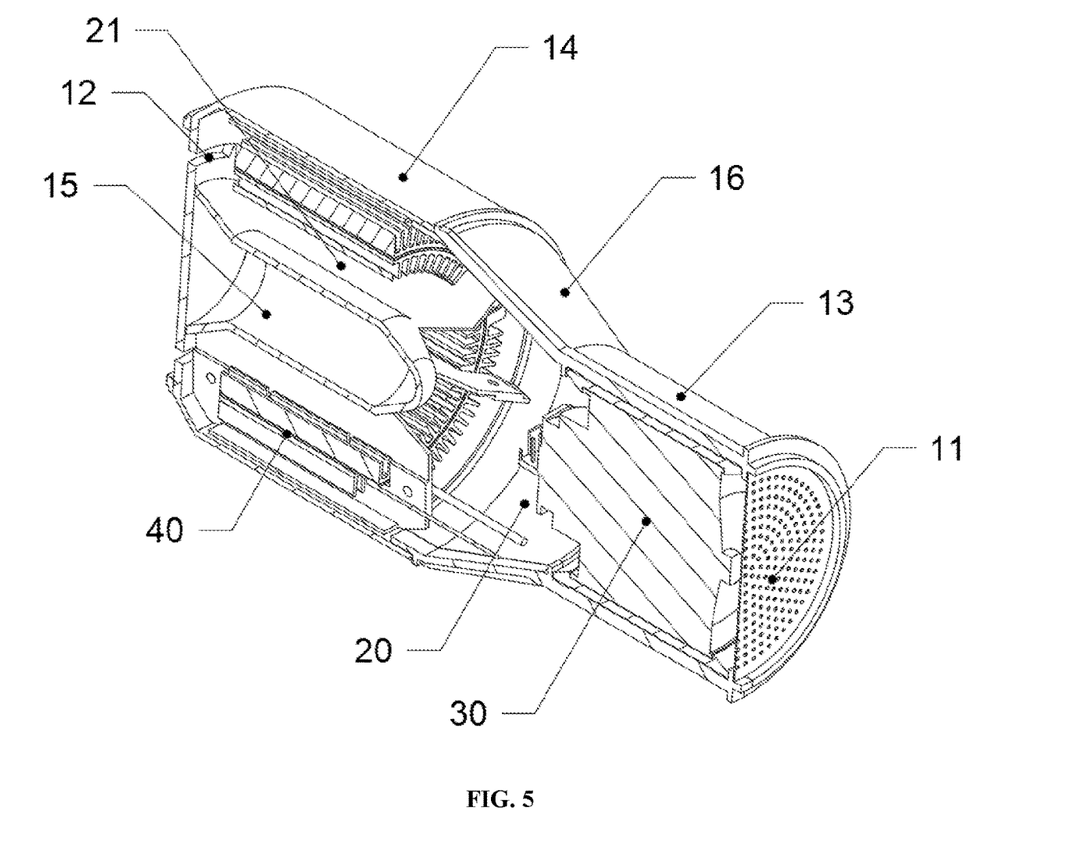
FIG. 5 is a schematic diagram of a sectional structure corresponding to a fluid channel portion in the present disclosure.

Referring to FIG. 2, FIG. 3, and FIG. 5, a first pipe body 13 abutted to the fluid inlet 11 and a second pipe body 14 abutted to the fluid outlet 12 are arranged in the body 10. The first pipe body 13 and the second pipe 14 body are connected with each other, so that the fluid flowing path 20 is formed inside the first pipe body 13 and the second pipe body 14, which can achieve an isolation effect on a circuit arranged inside the body 10, thereby improving the guide smoothness of the fluid flowing path 20 and further realizing a noise reduction function. The conveying mechanism 30 is arranged in the first pipe body 13, and the heating mechanism 40 is arranged in the second pipe body 14. A guide component 15 extending into the second pipe body 14 is arranged in the middle of the fluid outlet 12. The fluid outlet 12 is formed into the annular orifice structure through the guide component 15. The annular cavity 21 is formed inside the second pipe body 14 through the guide component 15. A diameter of the first pipe body 13 is less than a diameter of the second pipe body 14. A bevel transition end 16 is arranged between the first pipe body 13 and the second pipe body 14. The first pipe body 13 is hermetically connected with the second pipe body 14 through the bevel transition end 16, which improves the guided flowing effect on the fluid.

Referring to FIG. 2 to FIG. 5, the annular heat radiation assembly 41 includes a first annular body 411 and a second annular body 412 sleeving the first annular body 411. The annular heater 42 resists against and is fixed between the first annular body 411 and the second annular body 412. A plurality of uniformly arranged radiator fins 413 are arranged around an inner side of the first annular body 411 and an outer side of the second annular body 412. The far infrared ceramic coating layer is coated on the radiator fins 413. The radiator fins 413 are parallel to the fluid flowing path 20. In this way, the radiation effect of the annular heat radiation assembly 41 can be greatly improved. In addition, an enough surface area can be set to be applied with the far infrared ceramic coating layer, so that the far infrared wave generation efficiency can be greatly improved. In addition, the radiator fins 413 are parallel to the fluid flowing path 20, so that the obstruction effect on air can be reduced to the maximum extent. To securely mount the annular heater 42 and cause the annular heater 42 to be able to be resisted between the first annular body 411 and the second annular body 412, the second annular body 412 includes two semicircular portions 414 which are in abutting fit with each other. Matching portions are arranged at mutually abutted positions of the two semicircular portions 414. Screw structures are arranged on the matching portions to lock the two semicircular portions 414. A wiring gap 415 is formed in a rear end of one semicircular portion 414, and the annular heater 42 is connected to a wire through the wiring gap 415.

Referring to FIG. 2 to FIG. 6, the fixed support 44 includes several fixing assemblies 441. The several fixing assemblies 441 are circumferentially uniformly arranged on the annular heat radiation assembly 41 in a surrounding manner. The fixing assemblies 441 are abutted between the second pipe body 14 and the guide component 15, so that the annular heat radiation assembly 41 can be arranged in the annular cavity 21 in the suspended manner, to reduce the wind drag and fully achieve heat supply, far infrared radiation and negative ion generation efficiencies. The fixing assemblies 441 include a first fixing plate 442 and a second fixing plate 443. Fixing portions 444 are arranged at upper ends and lower ends of the first fixing plate 442 and the second fixing plate 443. The first fixing plate 442 and the second fixing plate 443 are fixedly connected through the fixing portions 444, so that a closed-loop structure surrounding the annular heat radiation assembly 41 is formed between the first fixing plate 442 and the second fixing plate 443. The first fixing plate 442 is located on an inner side of the annular heat radiation assembly 41 and is abutted to the guide component 15. The second fixing plate 443 is located on an outer side of the annular heat radiation assembly 41 and is abutted to the second pipe body 14.

Figure 4:
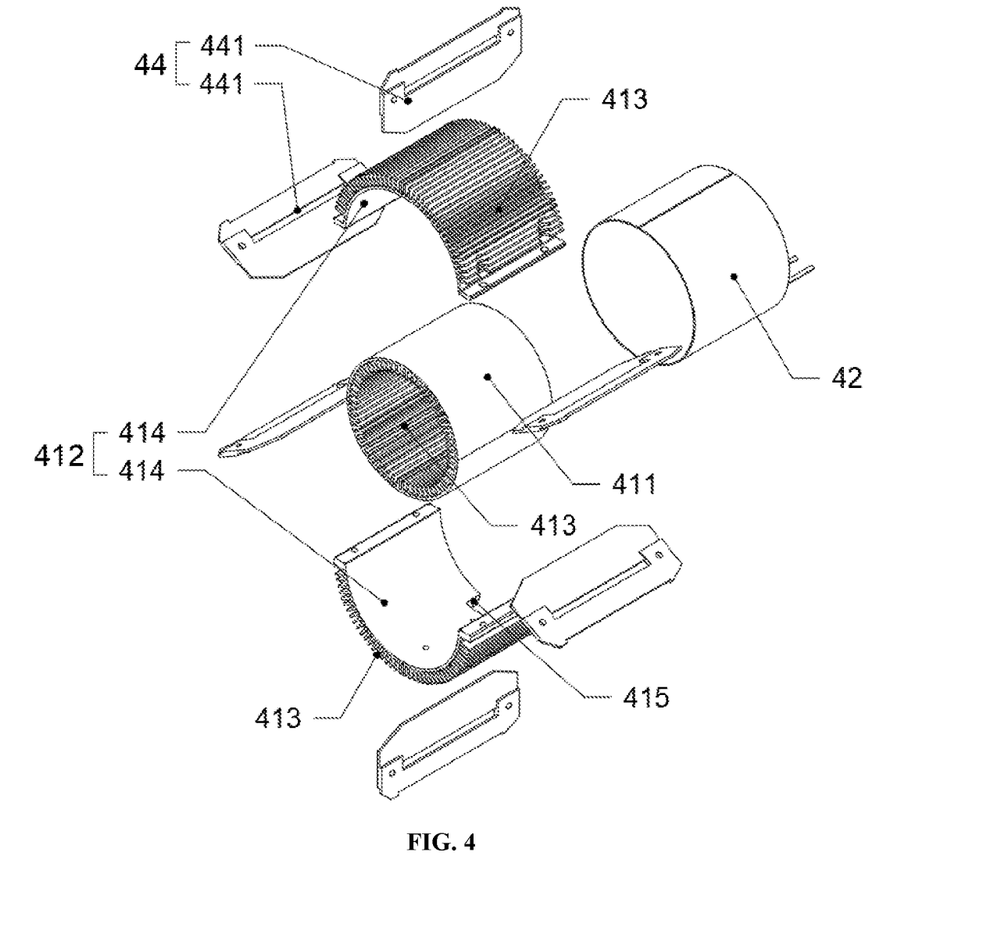
FIG. 4 is a schematic diagram of an exploded structure of a heating mechanism in the present disclosure.
Figure 6:
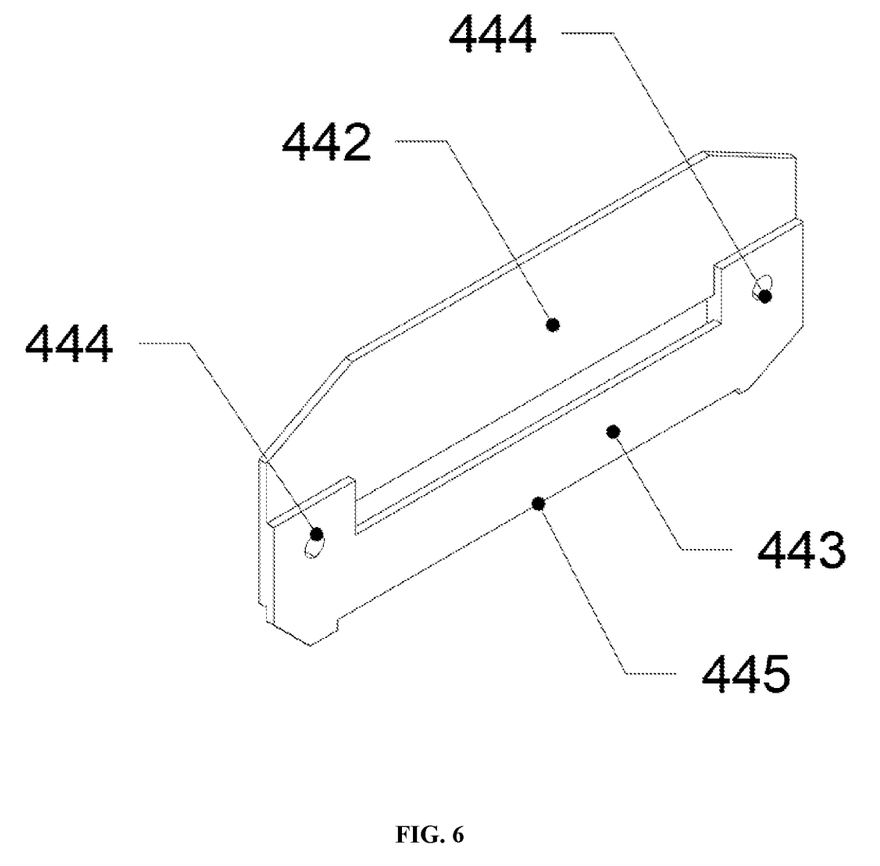
FIG. 6 is a schematic structural diagram of a fixing assembly in the present disclosure.

Referring to FIG. 3, FIG. 4, and FIG. 6, in order to reduce radiation of heat towards a periphery of the body 10 to achieve more efficient guided flowability of heat, a clamping gap 445 is formed in an end portion of each second fixing plate 443 abutted to the second pipe body 14. The plurality of fixing assemblies 441 are fixedly sleeved with heat insulation rings 45 through the clamping gaps 445. The heat insulation rings 45 are in abutting fit with the inner side of the second pipe body 14.

Figure 1:
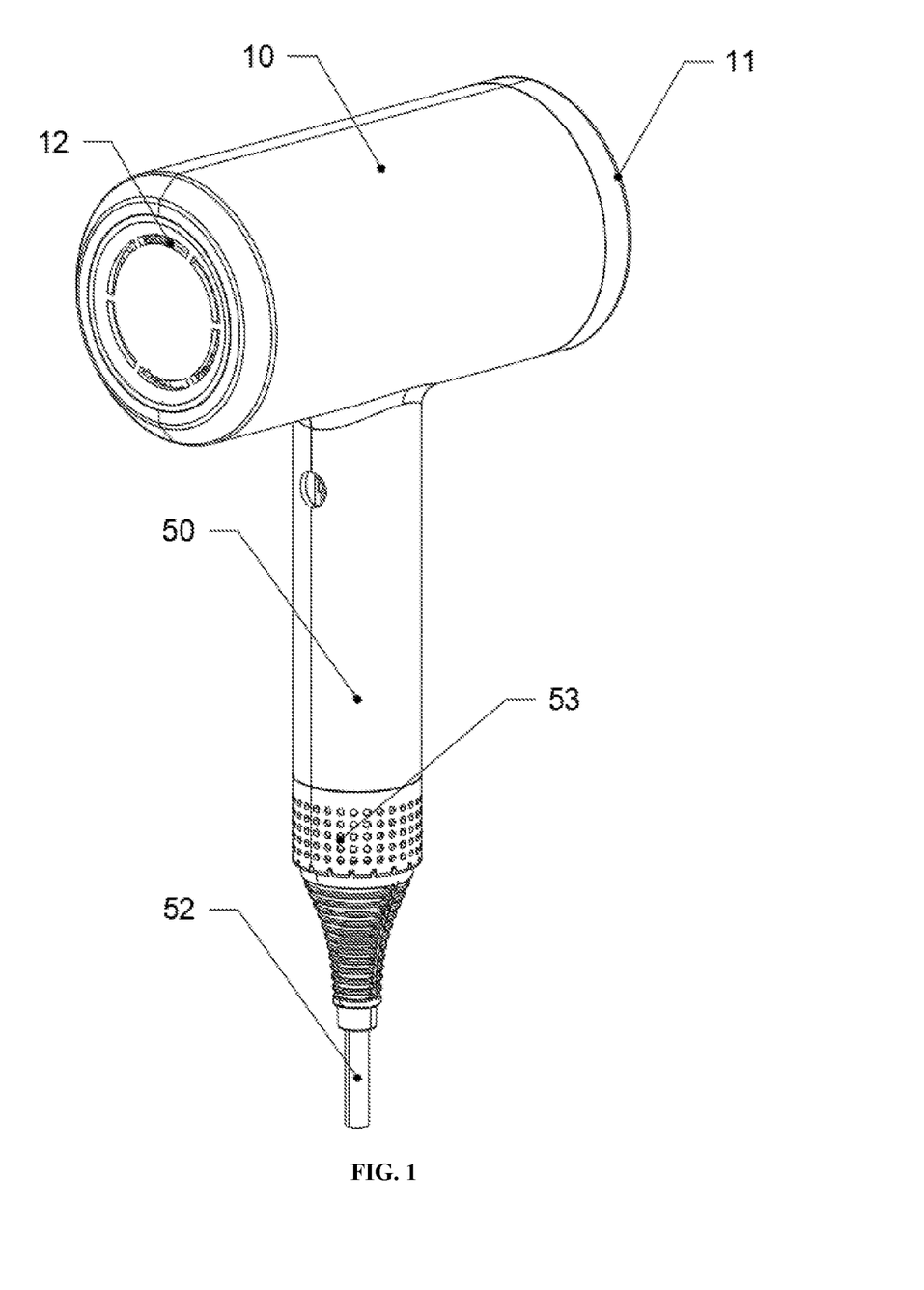
FIG. 1 is a schematic structural diagram of the present disclosure.

Referring to FIG. 1 to FIG. 3, a main control board 51 and a cable 52 are arranged in the handheld portion 50. A fixing ring 53 is arranged at a lower end of the handheld portion 50. The cable 52 is connected with the main control board 51 through the fixing ring 53. The main control board 51 is electrically connected to the conveying mechanism 30 and the annular heater 42 respectively to control an air supply volume of the conveying mechanism 30 and a temperature of the annular heater 42. Buttons are arranged on a surface of the handheld portion 50. The buttons are connected with the main control board 51 to start, stop, and control the hair dryer. The cable is electrically connected to the main control board 51 and is connected with a plug (not shown), to supply power to the hair dryer.

For those skilled in the art, it is apparent that the present disclosure is not limited to the details of the demonstrative embodiments mentioned above, and that the present disclosure can be realized in other specific forms without departing from the spirit or basic features of the present disclosure. Therefore, from any point of view, the embodiments should be regarded as exemplary and non-limiting. The scope of the present disclosure is defined by the appended claims rather than the above description. Therefore, all changes falling within the meanings and scope of equivalent elements of the claims are intended to be included in the present disclosure.

What is claimed is:

1. A novel far infrared hair dryer, comprising:
a body, which is provided with a fluid inlet formed in a rear end and a fluid outlet formed in a front end;
a fluid flowing path, which is arranged in the body and extends from the fluid inlet to the fluid outlet;
a conveying mechanism, which is arranged in the fluid flowing path and drives a fluid to flow from the fluid inlet to the fluid outlet; and
a heating mechanism, which is arranged in the fluid flowing path and is used for heating the fluid in the fluid flowing path,
wherein the fluid flowing path is provided with an annular cavity at a front section, and the fluid outlet is of an annular orifice structure abutted to the annular cavity; the heating mechanism is arranged in the annular cavity; and the heating mechanism comprises an annular heat radiation assembly wound in the annular cavity in a suspended manner, an annular heater embedded into the annular heat radiation assembly, a far infrared ceramic coating layer arranged on an outer surface of the annular heat radiation assembly, and a fixed support that is fixed in the annular cavity and is used for supporting the annular heat radiation assembly;
wherein the annular heat radiation assembly comprises a first annular body and a second annular body sleeving the first annular body; the annular heater is fixed between the first annular body and the second annular body; a plurality of uniformly arranged radiator fins are arranged around an inner side of the first annular body and an outer side of the second annular body; the far infrared ceramic coating layer is coated on the radiator fins; and the radiator fins are parallel to the fluid flowing path.

2. The novel far infrared hair dryer according to claim 1, wherein a first pipe body abutted to the fluid inlet and a second pipe body abutted to the fluid outlet are arranged in the body; the first pipe body and the second pipe body are connected with each other, so that the fluid flowing path is formed inside the first pipe body and the second pipe body; the conveying mechanism is arranged in the first pipe body; and the heating mechanism is arranged in the second pipe body.

3. The novel far infrared hair dryer according to claim 2, wherein a guide component extending into the second pipe body is arranged in a middle of the fluid outlet; the fluid outlet is formed into the annular orifice structure through the guide component; and the annular cavity is formed inside the second pipe body through the guide component.

4. The novel far infrared hair dryer according to claim 2, wherein a diameter of the first pipe body is less than a diameter of the second pipe body; a bevel transition end is arranged between the first pipe body and the second pipe body; and
the first pipe body is hermetically connected with the second pipe body through the bevel transition end.

5. The novel far infrared hair dryer according to claim 1, wherein the second annular body comprises two semicircular portions which are in abutting fit with each other; matching portions are arranged at mutually abutted positions of the two semicircular portions; and screw structures are arranged on the matching portions to lock the two semicircular portions.

6. The novel far infrared hair dryer according to claim 5, wherein a wiring gap is formed in a rear end of one of the two semicircular portions, and the annular heater is connected to a wire through the wiring gap.

7. The novel far infrared hair dryer according to claim 3, wherein the fixed support comprises several fixing assemblies; the several fixing assemblies are circumferentially uniformly arranged on the annular heat radiation assembly in a surrounding manner; and the fixing assemblies are abutted between the second pipe body and the guide component.

8. The novel far infrared hair dryer according to claim 7, wherein the fixing assemblies comprise a first fixing plate and a second fixing plate; fixing portions are arranged at upper ends and lower ends of the first fixing plate and the second fixing plate; the first fixing plate and the second fixing plate are fixedly connected through the fixing portions, so that a closed-loop structure surrounding the annular heat radiation assembly is formed between the first fixing plate and the second fixing plate; the first fixing plate is located on an inner side of the annular heat radiation assembly and is abutted to the guide component; and the second fixing plate is located on an outer side of the annular heat radiation assembly and is abutted to the second pipe body.

9. The novel far infrared hair dryer according to claim 8, wherein a clamping gap is formed in an end portion of each second fixing plate abutted to the second pipe body; the plurality of fixing assemblies are fixedly sleeved with heat insulation rings through the clamping gap; and the heat insulation rings are in abutting fit with the inner side of the second pipe body.

* * * * *